(12) United States Patent
Umemura et al.

(10) Patent No.: US 8,535,229 B2
(45) Date of Patent: Sep. 17, 2013

(54) ULTRASONOGRAPHIC DEVICE

(75) Inventors: Shin-ichiro Umemura, Sendai (JP); Takashi Azuma, Kawasaki (JP); Yuichi Miwa, Chofu (JP)

(73) Assignee: Hitachi Medical Corporation, Tokyo (JP)

( * ) Notice: Subject to any disclaimer, the term of this patent is extended or adjusted under 35 U.S.C. 154(b) by 940 days.

(21) Appl. No.: 11/719,770

(22) PCT Filed: Jul. 15, 2005

(86) PCT No.: PCT/JP2005/013153
§ 371 (c)(1),
(2), (4) Date: May 21, 2007

(87) PCT Pub. No.: WO2006/057092
PCT Pub. Date: Jun. 1, 2006

(65) Prior Publication Data
US 2008/0027318 A1    Jan. 31, 2008

(30) Foreign Application Priority Data
Nov. 24, 2004 (JP) ................................. 2004-338592

(51) Int. Cl.
*A61B 8/00* (2006.01)
(52) U.S. Cl.
USPC ............ 600/443; 600/407; 600/437; 600/444
(58) Field of Classification Search
USPC ................. 600/407, 437, 443, 447, 455, 458; 73/602, 625, 626
See application file for complete search history.

(56) References Cited

U.S. PATENT DOCUMENTS

| | | | | |
|---|---|---|---|---|
| 4,577,132 A | * | 3/1986 | Ohigashi et al. | 310/311 |
| 5,301,674 A | * | 4/1994 | Erikson et al. | 600/447 |
| 6,066,099 A | * | 5/2000 | Thomenius et al. | 600/447 |
| 6,673,016 B1 | * | 1/2004 | Bolorforosh et al. | 600/437 |
| 2004/0066708 A1 | | 4/2004 | Ogawa | |

FOREIGN PATENT DOCUMENTS

| | | |
|---|---|---|
| EP | 1 462 819 A2 | 9/2004 |
| JP | 2004-113694 | 4/2004 |

OTHER PUBLICATIONS

"Multiple-Focus Ultrasound Phased-Array Pattern Synthesis: Optimal Driving-Signal Distributions for Hyperthermia" by Ebbini et al. IEEE Trans Ultra Ferro and Freq Control. vol. 36, No. 5, pp. 540-548, 1989.*
New Medical Ultrasonics, vol. 1, Basics of Medical Ultrasonic Waves, May 15, 2000, pp. 40 to 41.
K. Sasaki, et al., "Effect of Split-Focus Approach on Producing Larger Coagulation in Swine Liver", Ultrasound in Medicine and Biology, vol. 29, No. 4, pp. 591-599, 2003.
S. Umemura, et al., "Non-Cylindrical Transmission Focusing for Large Depth of Field", Proceedings of 2002 IEEE Ultrasonics Symposium, vol. 2, pp. 1721-1724, 2002.

* cited by examiner

*Primary Examiner* — Tse Chen
*Assistant Examiner* — Jason Ip
(74) *Attorney, Agent, or Firm* — Antonelli, Terry, Stout & Kraus, LLP.

(57) ABSTRACT

An ultrasonographic technique capable of forming a transmission beam enabling multi-beam transmission/reception of identical transmission sensitivity. An ultrasonographic device for imaging inside of an examinee includes a transmitter for transmitting an ultrasonic pulse signal from an ultrasonic element array to the examinee, and a receiver for receiving the ultrasonic pulse reflected from the examinee. The transmitter transmits an ultrasonic pulse signal having a plurality of peaks of substantially equal transmission intensity in the azimuth direction and a trace in the depth direction of each peak as a substantially straight line, from a transmission opening of the ultrasonic element array to the examinee.

7 Claims, 10 Drawing Sheets

ULTRASONOGRAPHIC DEVICE

TECHNICAL FIELD

The present invention relates to an ultrasonographic technique for imaging the inside of an examinee such as a living body by transmitting/receiving ultrasonic waves to/from the examinee.

BACKGROUND ART

An ultrasonic diagnostic apparatus using the pulse echo method of imaging the inside of a living body by transmitting/receiving pulse ultrasonic waves to/from the living body is widely used for medical diagnosis as well as X-ray CT and MRI. The maximum advantage of ultrasonic diagnosis which is not in the other image diagnostic modalities such as X-ray CT and MRI is high imaging speed that enables real-time image display. Specifically, the speed is as high as time resolution of human vision, that is, imaging speed at which an image can be updated approximately every 30 ms. Further, to observe the movement of the valve of the heart by low-speed reproduction, time resolution of acquiring an image every 15 ms can be even realized.

On the other hand, in the spatial resolution achieved by the pulse echo method, the distance resolution in the depth direction is obtained by resolution of time required for an ultrasonic pulse to travel to and back from a reflector. The propagation speed of an ultrasonic wave in a living body is 1500 m/s which is almost equal to that in water. Consequently, when the ultrasonic frequency is a few MHz or higher, the distance resolution of about 1 mm can be easily obtained by time resolution of about 1 μs.

On the other hand, the spatial resolution in the direction orthogonal to the depth resolution, that is, the azimuth resolution is obtained by focusing a transmission or reception wave. To obtain the azimuth resolution equal to or less than a few times as high as the wavelength of an ultrasonic wave, strong focusing to an extent that F number becomes almost 1 is necessary. As a result, the focal area depth corresponding to depth of field in the case of a camera becomes as low as a few wavelengths. It corresponds to about 1 μs of round-trip propagation time of an ultrasonic wave. By the dramatic advance of the high-speed electronic circuit technique of recent years, the reception focal length can be changed during the period in which an ultrasonic wave propagates in this distance. This is a so-called dynamic focus technique (refer to, for example, "New Medical Ultrasonics, Vol. 1, Basics of Medical Ultrasonic Waves, May 15, 2000, pp 40 to 41).

DISCLOSURE OF THE INVENTION

Problems to be Solved by the Invention

By the dynamic focusing technique realizing real-time reception, reception of a focused image can be always realized. However, the problem of transmission focusing cannot be solved only by increasing the speed of an electronic circuit.

In the transmission focusing, it is necessary to physically form a wave front. Therefore, when priority is placed on the azimuth resolution and strong focusing to an extent that F number becomes almost 1 is used, transmission has to be performed a number of times at each of which an imaging face of 1 mm 2 is obtained. With the focusing, real-time imaging is impossible. Consequently, in an ultrasonic diagnosis apparatus at present, transmission with large F number is performed so that focusing is not too strong at the sacrifice of azimuth resolution to some extent. With configuration of imaging an area in which a single transmission beam propagates by basic transmission of one beam, so imaging speed is assured. In such a configuration, the azimuth resolution in the reception focusing is much higher than that in the transmission focusing. As shown in FIG. 1, by generating two transmit/receive beams per transmission beam, imaging speed which is about twice as high as the imaging speed can be realized. As illustrated in the Figures, the solid dots pertain to a transmission geometry.

To realize imaging speed which is four times as high as that in the case of setting one receiving beam for one transmitting beam, as shown in FIG. 2, an attempt is made to generate four receiving beams per transmission beam. In the configuration of FIG. 1, the sensitivity of two reception beams is the same. On the other hand, in the configuration of FIG. 2, the difference occurs between the sensitivity of two reception beams close to the center of a transmission beam and that of two reception beams far from the center. If there is an allowable variation for the image display dynamic range within the transmission/reception S/N ratio then the transmission/reception sensitivities can be made equal to each other by adjusting the reception sensitivity.

However, with parameters in which there is no allowance in the transmission/reception S/N ratio unlike imaging of a deep part in a living body and noise is displayed in an image, the difference between the transmission/reception sensitivities appears in an image. Specifically, a problem occurs such that the noise level of two reception beams far from the center of the transmission beam is higher than that of two reception beams close to the center, and noise is displayed in stripes in a whole image.

In view of the circumstances, an object of the present invention is to provide an ultrasonographic technique capable of generating a transmission beam enabling multi-beam transmission/reception of identical transmission sensitivity.

There is a method of generating a transmission beam having two lobes as shown in FIG. 3(a) as a transmission beam with which four reception beams having the same transmission sensitivity can be generated. Such a transmission beam generating method is known as a split-focus method that dramatically improves throughput of focusing ultrasonic treatment (reference document: Ultrasound in Medicine and Biology, Vol. 29, No. 4, pp. 591-599). In the method, a transmission aperture is divided into two parts. By supplying transmission signals having opposite signs (positive and negative signs) obtained by inverting the phase to the divided aperture parts, the divided aperture parts are driven. By the operations, positive and negative sound pressure level distributions which are point-symmetrical with respect to the center axis as shown in FIG. 3(b) are formed. As an ultrasonic intensity distribution, two lobes which are line-symmetrical with respect to the center axis as shown in FIG. 3(a) are formed.

Even if the method is employed as it is, however, the problem cannot be solved. When loci of four points having equal transmission sensitivity at depths of predetermined distances from a probe are obtained while changing the distances from the probe, the loci have shapes such that double curves in an X shape constricted around focal lengths as shown by solid lines in a contour diagram in FIG. 4 are resulted. Such scan lines in constricted curves are extremely improper for the purpose of efficiently scanning and imaging a predetermined two-dimensional or three-dimensional area. Such transmission sound fields can be used for the purpose of simultaneously forming four transmission/reception points having equal transmission sensitivity in the azimuth direction only in the area around the transmission focal lengths. However, to scan the whole imaging purpose depth, the transmission/reception beam having linear equal transmission sensitivity suitable for the scan cannot be generated, so that it is extremely improper.

On the other hand, as a method of generating transmission beams having almost constant beam widths irrespective of distances from a probe, there is a known method of optimizing a transmission wave front so as to make the transmission beam widths almost constant at the time of forming a non-cylindrical or aspherical transmission wave front by using a one-dimensional array (reference document: Proceedings of 2002 IEEE Ultrasonics Symposium, Vol. 2, pp. 1721-1724). The method is realized by setting local focal lengths on a transmission aperture so as to be short in a center portion of the transmission aperture and to be long in end portions in the transmission aperture, in other words, by controlling the wave fronts of the ultrasonic pulse signals transmitted from the transmission aperture so that the curvature in the center portion of the transmission aperture is higher than that in the portion other than the center portion.

There may be various methods of gradually changing the local focal length on a transmission aperture, and one example will be described below. It is assumed that the transmission beam widths are desired to be made constant in a range from a near focal length $f_0$ to a far focal length $f_1$ from a probe. When a coordinate on the transmission aperture is expressed as a value "x" derived by normalizing a distance with a distance from the center of the transmission aperture to one end of the aperture, a control is performed so that a local focal length f(x) at "x" changes as a Lorentz response type function as follows.

$$f(x) = f_1 - \left(\frac{1+\alpha}{1+\alpha x^2} - 1\right)\frac{f_1 - f_0}{\alpha} \quad (1)$$

FIG. 5 shows f(x) and transmission sound fields at ultrasonic frequency of 3 MHz with respect to the case where the near focal length f0=40 mm and the far local length f1=160 mm. Weights of a Gaussian function type placed on the transmission aperture are also shown. A main lobe having a uniform width is formed in a wide range in the propagation direction. However, although the width is uniform in the depth direction, a section of a beam in one depth is as shown in FIG. 2, and the number of points at which the transmission sensitivity is the same is only two. Therefore, when the method is employed as it is, the problem cannot be solved.

Means for Solving the Problem

According to the present invention, the methods are developed and the split focusing technique is employed, thereby enabling four linear transmission/reception beams having equal transmission sensitivity and adapted for imaging scan lines to be formed in the case of two-dimensional imaging using a one-dimensional transducer array, and enabling 16 linear transmission/reception beams to be formed in the case of three-dimensional imaging using a two-dimensional transducer. The imaging scan lines are parallel straight lines in the case of a linear scan, radial straight lines having a common intersecting point on the outside of an imaging range in the case of a convex scan, and radial straight lines having a common intersecting point at one end of the imaging range in the case of a sector scan.

Representative configuration examples of the ultrasonographic device according to the present invention will be described below.

(1) An ultrasonographic device for imaging the inside of an examinee, including: transmission means for transmitting an ultrasonic pulse signal from an ultrasonic element array to an examinee; and reception means for receiving the ultrasonic pulse reflected from the examinee, wherein the transmission means transmits an ultrasonic pulse signal from a transmission aperture of the ultrasonic element array to the examinee, the ultrasonic pulse signal having a plurality of peaks with substantially equal transmission intensity in the azimuth direction, and a locus in the depth direction of each peak being a substantially straight line.

(2) An ultrasonographic device for imaging the inside of an examinee, including: transmission means for transmitting an ultrasonic pulse signal from an ultrasonic element array to an examinee; and reception means for receiving the ultrasonic pulse reflected from the examinee, wherein the transmission means generates an ultrasonic pulse signal having at least four peaks with substantially equal transmission intensity in the azimuth direction per transmission beam by weighting the transmission aperture of the ultrasonic element array and controlling a local focal length on the ultrasonic element array, and in which a locus in the depth direction of each of the peaks substantially becomes a straight line, and the transmission means transmits the ultrasonic pulse signal from the transmission aperture to the examinee.

(3) In the ultrasonographic device having the configuration, by weighting the transmission aperture of the ultrasonic element array and controlling a local focal length on the ultrasonic element array, the transmission means generates an ultrasonic pulse signal having a plurality of peaks with substantially equal transmission intensity in the azimuth direction and in which a locus in the depth direction of each of the peaks substantially becomes a straight line. The transmission means transmits the ultrasonic pulse signal from the transmission aperture to the examinee.

(4) In the ultrasonographic device having the configuration, the transmission means transmits the ultrasonic pulse signal by using a delay time weight for controlling delay time of a drive signal for driving any of ultrasonic elements constructing the transmission aperture so that a wave front of the ultrasonic pulse signal transmitted from the transmission aperture has a non-cylindrical shape or an aspherical shape, and an amplitude weight for controlling a signed amplitude of a drive signal for driving the ultrasonic element so as to form a plurality of focal points on each of focal planes in positions of a plurality of focal lengths.

Although it is not easy to analyze a sound field in a position out of a focal plane whereas a sound field on a focal plane is easily obtained also with respect to normal ultrasonic sound fields focused to one point, a sound field according to the present invention does not have a simple single focal length, so that it is difficult to analyze the sound field in all of positions. Consequently, in the embodiments described later, a method of obtaining a sound field by numerical calculation and capable of generating a transmission sound field adapted to a purpose will be described in detail hereinbelow with reference to the drawings.

Effect of the Invention

According to the present invention, an ultrasonic diagnosis apparatus capable of generating a transmission beam that enables transmission/reception of multiple beams having equal transmission sensitivity can be realized.

BEST MODE FOR CARRYING OUT THE INVENTION

FIG. 6 is a block diagram showing a typical configuration of an ultrasonic diagnosing apparatus based on the pulse echo method to which the invention is applied.

A transmit/receive sequence controller 6 selects between transmission of a plurality of transmission beams having equal transmission sensitivity adapted to high-speed image capturing and transmission of a transmission beam having excellent resolution and S/N ratio only near a specific focal length. On the basis of the selection, a selector 4 for transmission delay time and weighting function selects corresponding transmission focus delay data and waveform weighting data from a memory 5 of transmission delay time and weighting function.

In the memory 5 of transmission delay time and weighting function, for example, transmission focus delay and weighting function data for a 3D linear scan (5-1), a 3D sector scan (5-2), a 2D linear scan (5-3), a 2D sector scan (5-4), and the like are recorded in advance. A set of data pieces is selected by the selector 4 for transmission delay time and weighting function.

On the basis of the data, a transmission beam former 3 supplies a transmission signal provided with a signed amplitude corresponding to a transmission waveform to elements selected from a group of elements constructing an ultrasonic transducer array (ultrasonic probe) 1 by transmit/receive selection switches 2 at a controlled timing, and the elements are driven. As a result, a transmission wave front having directivity is transmitted into a living body.

The transmission ultrasonic pulse transmitted from the ultrasonic probe 1 into the living body is reflected by a tissue in the living body. A part of the reflected pulse returns to the ultrasonic probe 1 and is received by the elements constructing the ultrasonic probe 1. Signals of the elements selected by the transmit/receive selection switches 2 among the received signals are supplied to a receiving beam former 10.

In the receiving beam former 10, an input signal from each of the elements is amplified by a preamplifier, an amplified signal is A/D converted, and the resultant digital signal is temporarily stored in a memory. More specifically, immediately after the preamplifier, generally, the signal passes through a TGC amplifier controlled so that amplification factor gradually increases with time elapsed since transmission and the amplified signal is A/D converted.

This is a process for compensating a decrease in the amplitude of a reception signal in proportion to a time elapsed since transmission in correspondence with an attenuation of the ultrasonic wave propagating in the living body in proportion to propagation distance, so that the magnitude of the signal amplitude at the entrance of an A/D converter is maintained in a predetermined range.

The process prevents decrease in a signal dynamic range caused by amplification quantization in the A/D conversion. In addition, as it is known, by passing the signal through a band limiting filter before the A/D conversion, aliasing caused by time-base quantization in the A/D conversion can be prevented.

To obtain reception wave directivity, it is necessary to obtain a convergence effect by giving a kind of delay according to the position of each of elements to a reception signal of each of the elements temporarily stored in the memory and adding the delayed signals. The optimum values of delay time to be given to signals of the elements vary according to the reception wave focal length. The optimum value of the reception wave focal length for obtaining an excellent pulse echo image increases in proportion to time elapsed since transmission and sound velocity. Therefore, it is desirable to use the dynamic focus receiving method of changing the delay time to be given to a signal of an element in accordance with time elapsed since transmission. The method can be relatively easily realized by a control at the time of reading or writing in the configuration of temporarily storing reception signals of the elements into the memory, reading the signals, and adding the signals.

An output signal of the receiving beam former 10 passes through a filter 11, and an envelope signal is detected in an envelope detector 12. The envelope signal is logarithmically compressed, thereby obtaining a display signal. The display signal is converted by a scan converter 13 to a two-dimensional image or, in some instances, three-dimensional image. The image is displayed on a CRT or, in some instances, a liquid crystal display 14.

An example of a transmission sound field of the present invention generated by using the ultrasonic diagnosis apparatus having the above configuration will be described below.

FIG. 7 shows transmission sound fields generated for a linear scan using a one-dimensional array transducer. In the example, as the transmission aperture weight, a weight obtained by differentiating a Gaussian function once as shown in the diagram is used. A weight function w(x) relates to a coordinate "x" on an array, calculated by excluding a normalization constant, and can be expressed as follows.

$$w(x) = x\exp(-\beta x^2) \qquad (2)$$

To form a transmit wave front of a non-cylindrical shape, as shown in the diagram, in a manner similar to the case of FIG. 5, local focal length is set to 40 mm in a center of the transmission aperture, gradually increases to a Lorentz resonance function type toward an end of the aperture, and is set to 160 mm at both ends of the transmission aperture. In the example, the focal length is changed to the Lorentz function shape expressed by the equation (1).

By tuning a combination of a parameter $\beta$ of a differential Gaussian function determining spread of the transmission aperture weight and a parameter $\alpha$ of the Lorentz resonance function determining tendency of a change in the local focal length, two lobes parallel with scan lines of a linear scan ranging from distance 40 mm to 140 mm as shown by dotted lines in the diagram can be formed. By generating two lobes parallel with scan lines, as described above with reference to FIG. 3, four transmission/reception scan lines having equal transmission sensitivity can be obtained.

FIG. 8 shows transmission sound fields generated for a sector scan by using a one-dimensional array transducer. As shown in the diagram, the transmission aperture weight and local focal length are changed to a differential Gaussian function shape and a Lorentz resonance function shape, respectively, in a manner similar to the case of FIG. 7. By tuning a combination of the parameter $\beta$ of the differential Gaussian function determining spread of the transmission aperture weight and the parameter $\alpha$ of the Lorentz resonance function determining tendency of a change in the local focal length, two lobes parallel with scan lines of a sector scan and forming a predetermined angle can be generated in a range from a distance of 50 mm to 180 mm as shown by dotted lines in the diagram. Consequently, four scan lines for a sector scan having equal transmission sensitivity can be obtained.

Although not shown, a scan line array of a convex scan is positioned between the linear scan and the sector scan. By tuning the transmission aperture weight and the local focal length, obviously, a transmission beam having lobes parallel with scan lines of a convex scan can be generated. In the foregoing embodiment, a transmission aperture weight is calculated on the basis of a Gaussian function, and the control on the local focal length is performed on the basis of the Lorentz function but, obviously, the present invention is not limited to the configurations.

FIGS. 9 and 10 show transmission sound fields generated for a sector scan by using a two-dimensional array transducer. Although the transmission aperture weight is basically the same as that in the cases of FIGS. 7 and 8, a function as a product of weights obtained by differentiating a Gaussian function once is used. A weight function w(x, y) can be expressed by excluding a normalization constant when coordinates on an array are x and y.

$$w(x,y) = xy \exp(-\beta_1 x^2 - \beta_2 y^2) \quad (3)$$

The local focal length is also changed to the form of a Lorentz resonance function in a manner similar to the case of FIGS. 7 and 8. The function can be expressed as a function of coordinates x and y on an array as follows.

$$f(x, y) = f_1 - \left( \frac{1 + \alpha_1 + \alpha_2}{1 + \alpha_1 x^2 + \alpha_2 y^2} - 1 \right) \frac{f_1 - f_0}{\alpha_1 + \alpha_2} \quad (4)$$

It was confirmed by a numerical calculation simulation that, by tuning a combination of parameters $\beta_1$ and $\beta_2$ of a differential Gaussian function determining spread of the transmission aperture weight and parameters $\alpha_1$ and $\alpha_2$ of the Lorentz resonance function determining tendency of a change in the local focal length, four lobes parallel with scan lines of a sector scan and forming a predetermined angle can be formed in a range from distance 50 mm to 180 mm. Since it is difficult to show three-dimensional sound fields in a two-dimensional drawing, it is not shown.

FIG. 9 shows an ultrasonic wave intensity distribution of four lobes in distance 80 mm of a transmission beam for a sector scan in the case of performing three-dimensional imaging using a two-dimensional array transducer. FIG. 10 shows a section in the direction of a diagonal line of the transmission beam for the sector scan using the ultrasonic wave intensity distribution in the propagation distance direction as the function of distance.

FIG. 11 is a diagram showing the positional relations of four lobes formed in the case of performing three-dimensional imaging using a two-dimensional array transducer and 16 transmission/reception beams having equal transmission sensitivity. As described above, when four lobes can be generated, as shown on a transmission sensitivity contour drawing in FIG. 11, 16 scan lines for the sector scan having substantially the same transmission sensitivity can be obtained. The transmission beams with which multi-beam transmission/reception having equal transmission sensitivity is enabled are particularly suitable for three-dimensional ultrasonic imaging of a heart or the like requesting particularly high speed of imaging.

As specifically described above, according to the invention, in two-dimensional imaging using a one-dimensional array probe, a transmission beam with which four transmission/reception beams having equal transmission sensitivity are generated can be generated. Further, in three-dimensional imaging using a two-dimensional array probe, one transmission beam with which 16 transmission/reception beams having equal transmission sensitivity are generated can be generated. Thus, high-speed image data acquisition requested for three-dimensional imaging can be realized.

Industrial Applicability

The ultrasonographic technique according to the present invention realizes improvement in high speed as an advantage of ultrasonic imaging while maintaining high picture quality, and is extremely suitable for, particularly, three-dimensional imaging of a heart or the like requiring high speed. Therefore, the significance in the medical and industrial fields of the present invention is great.

DESCRIPTION OF REFERENCE NUMERALS

Figure 1:
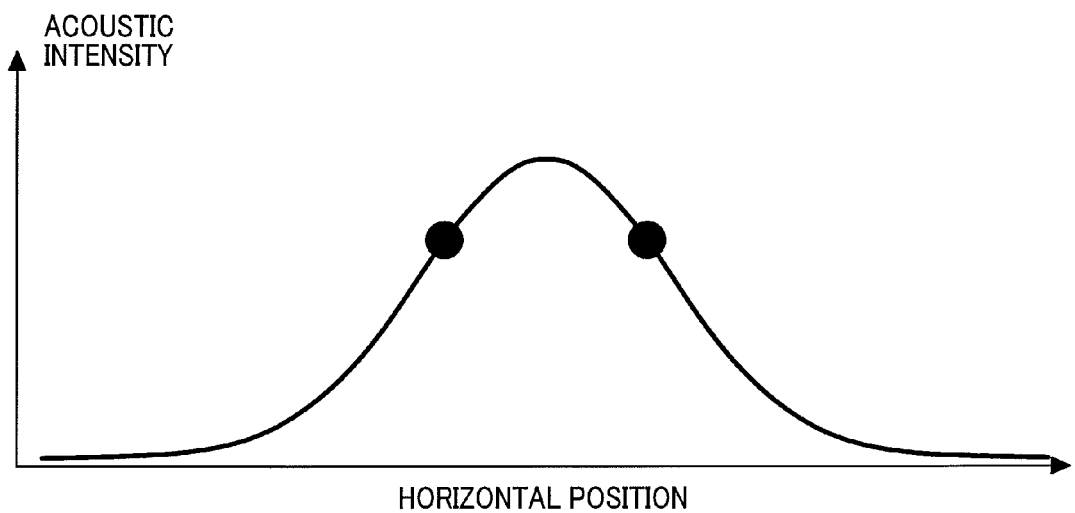
FIG. 1 is a diagram showing the positional relations of a conventional transmission beam and two transmission/reception beams.
Figure 2:
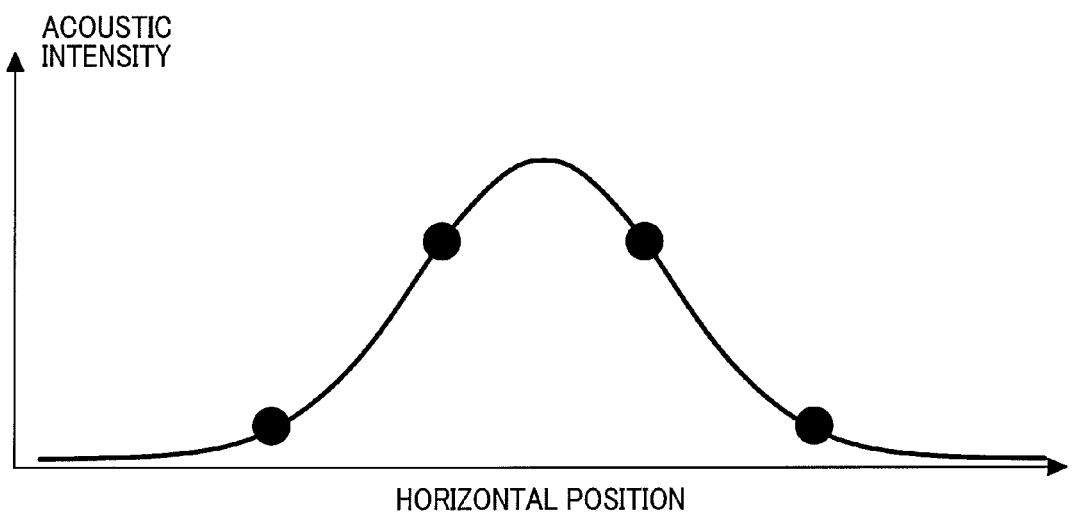
FIG. 2 is a diagram showing the positional relations of a conventional transmission beam and four transmission/reception beams.
Figure 3:
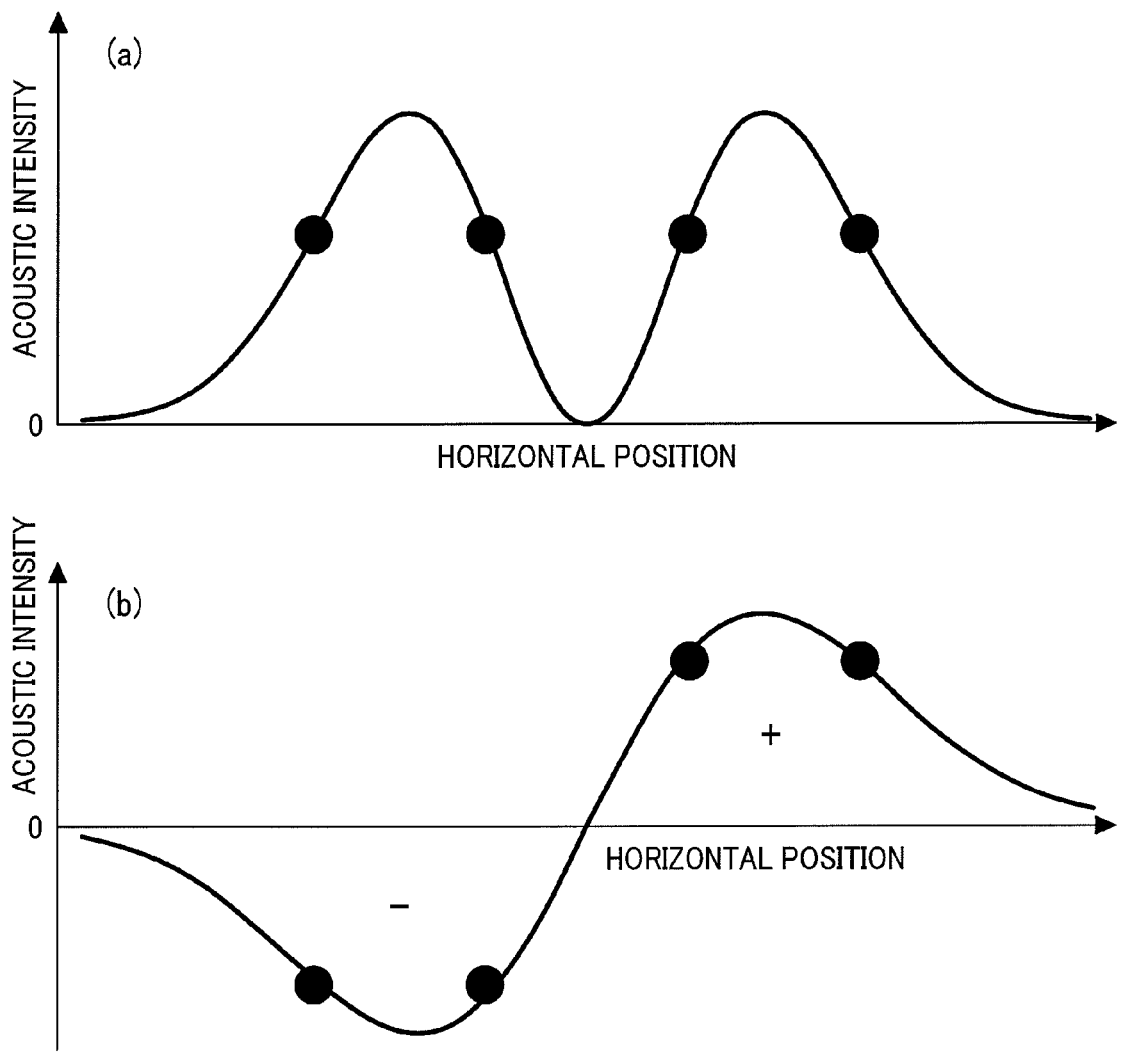
FIG. 3 is a diagram showing the positional relations of a transmission beam and four transmission/reception beams according to the split focus technique.
Figure 4:
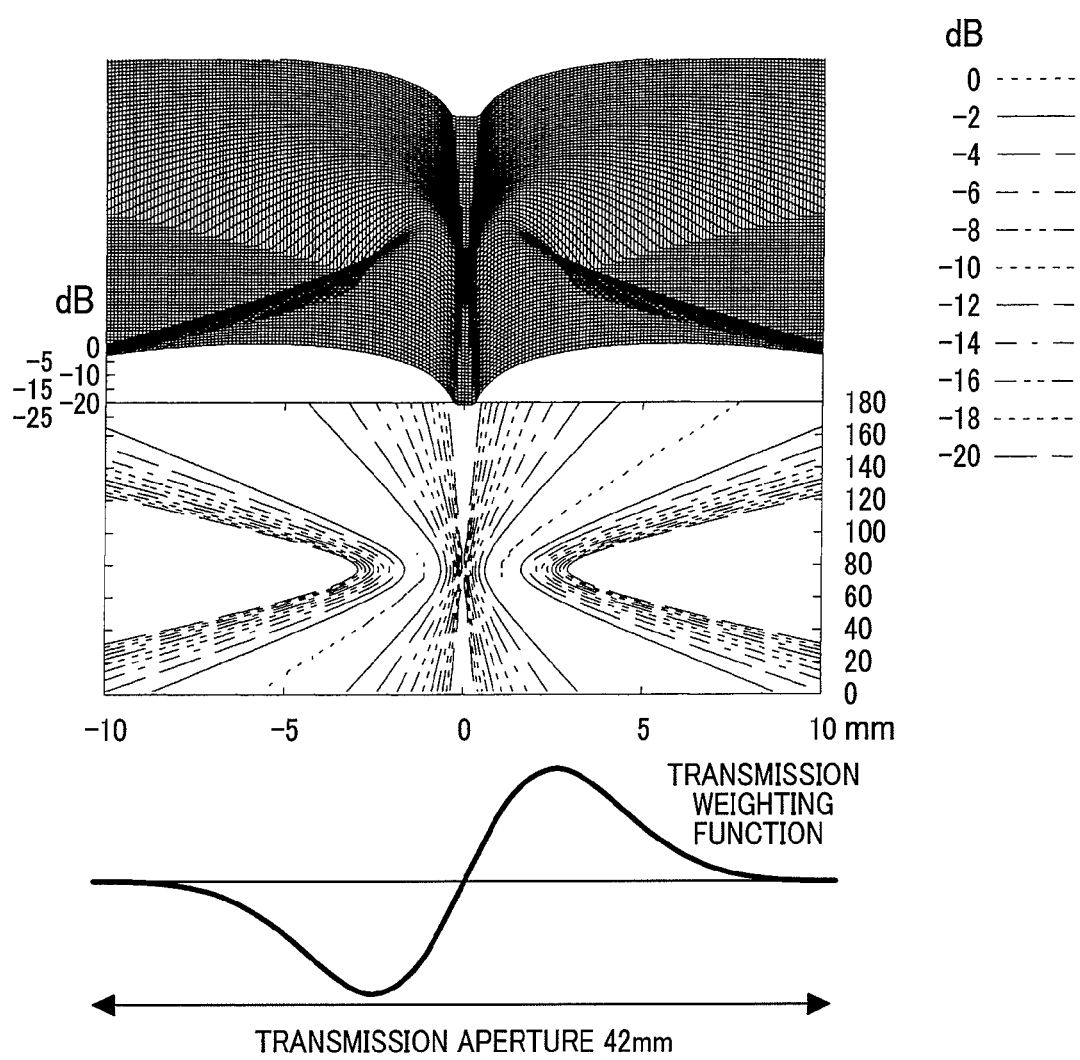
FIG. 4 is a diagram showing an ultrasonic wave intensity distribution of transmission beams according to the split focus technique.
Figure 5:
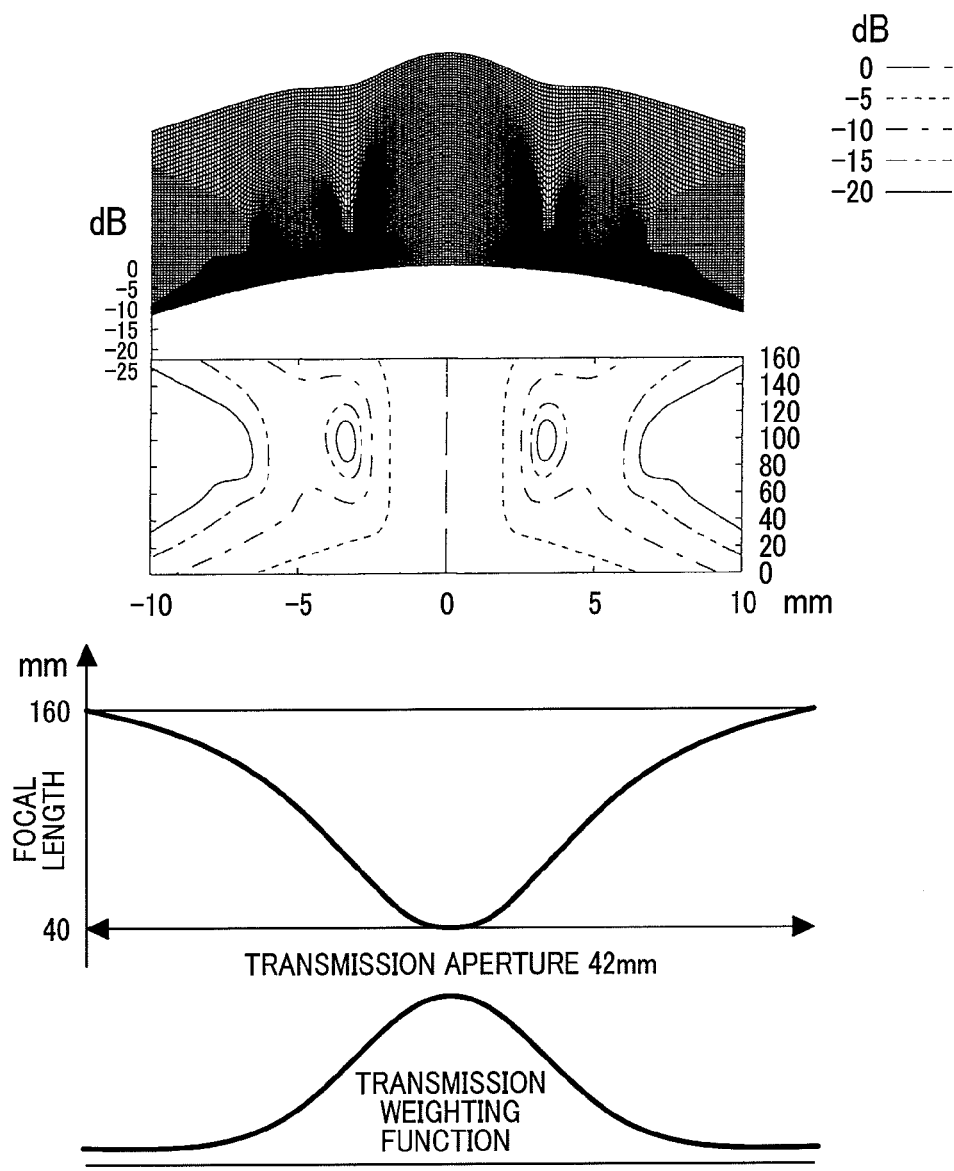
FIG. 5 is a diagram showing an ultrasonic wave intensity distribution of transmission beams according to a non-cylindrical focus technique.
Figure 6:
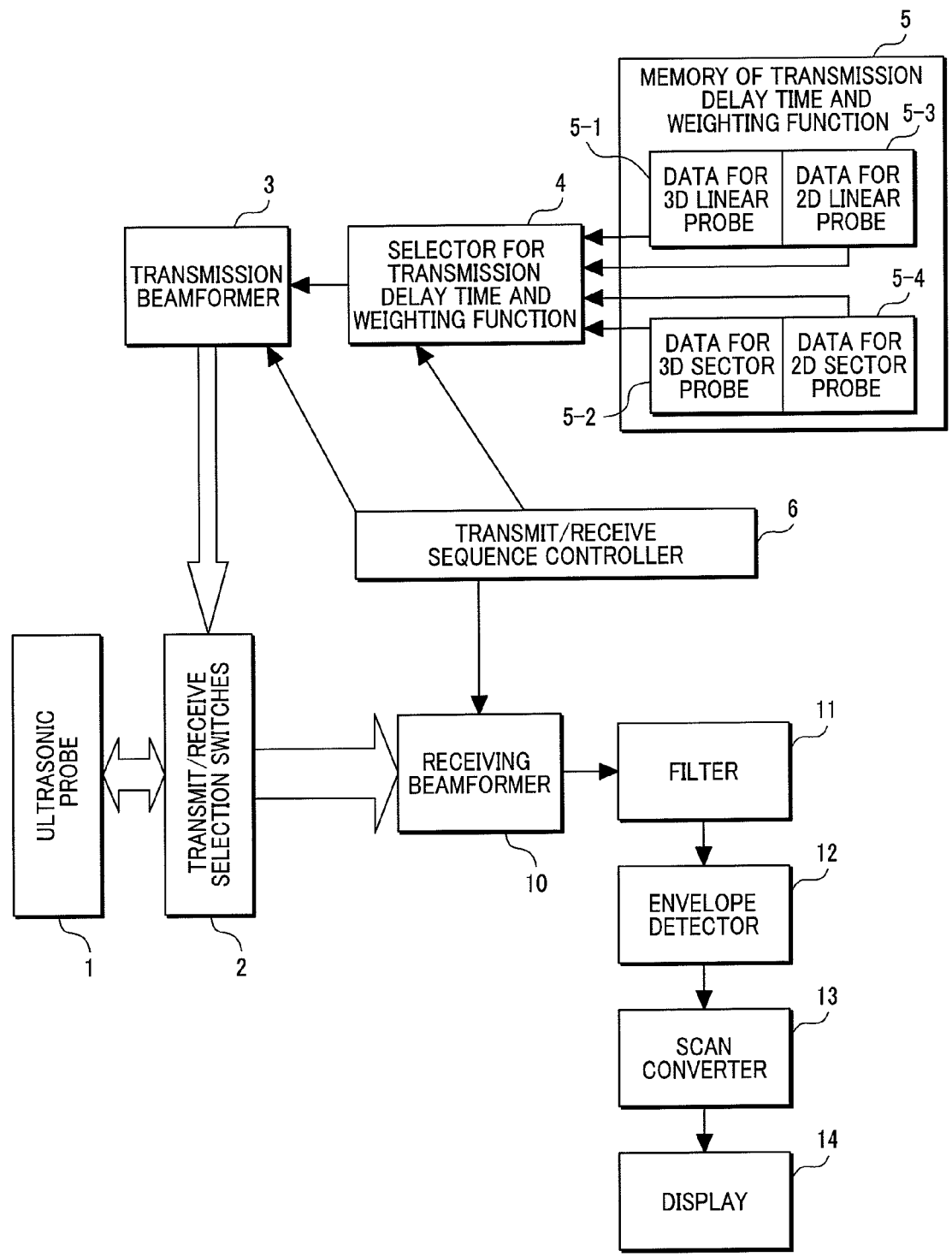
FIG. 6 is a block diagram showing the configuration of an ultrasonic diagnosis apparatus as an embodiment of the invention.
Figure 7:
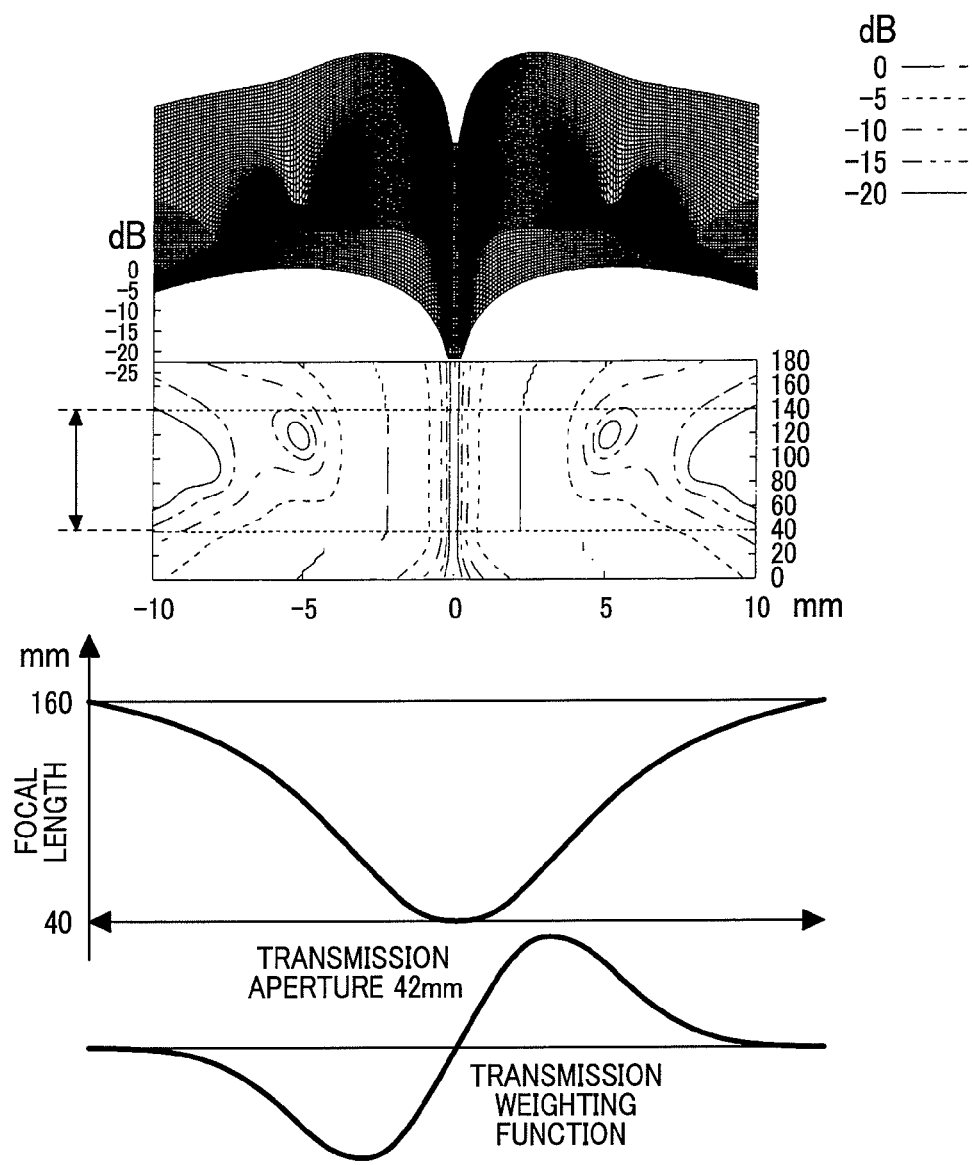
FIG. 7 is a diagram showing an ultrasonic wave intensity distribution (including transmission aperture weight and local focal length) of transmission beams for a linear scan according to the invention.
Figure 8:
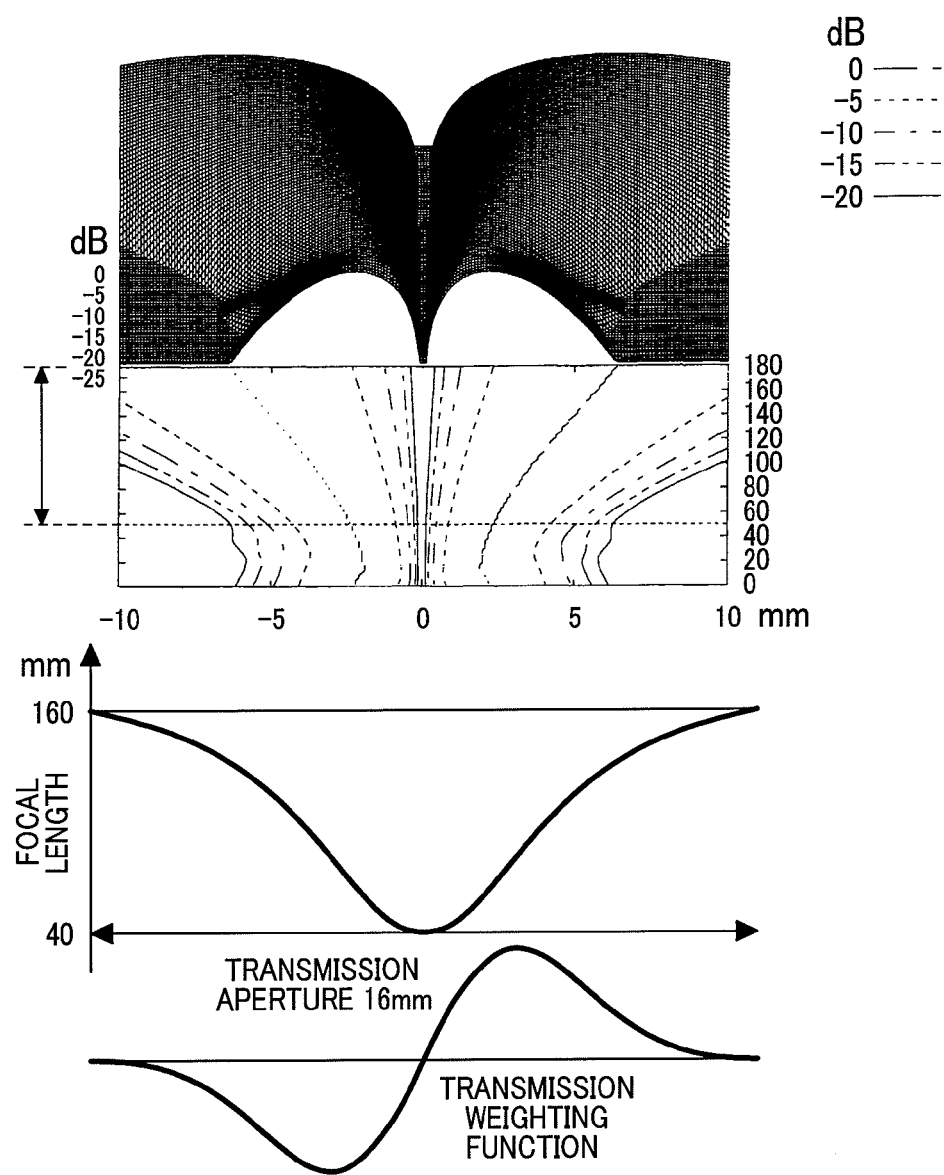
FIG. 8 is a diagram showing an ultrasonic wave intensity distribution (including transmission aperture weight and local focal length) of transmission beams for the sector scan according to the invention.
Figure 9:
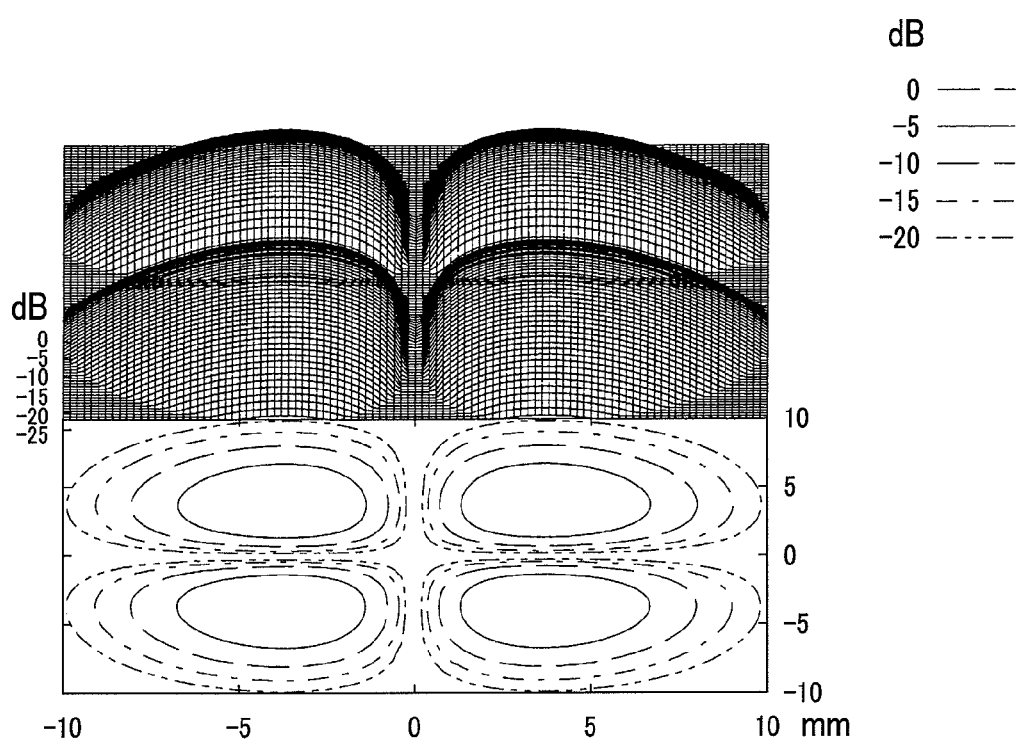
FIG. 9 is a diagram showing an ultrasonic wave intensity distribution at distance of 80 mm of a transmission beam for the sector scan in the case of performing three-dimensional imaging using a two-dimensional array transducer according to the invention.
Figure 10:
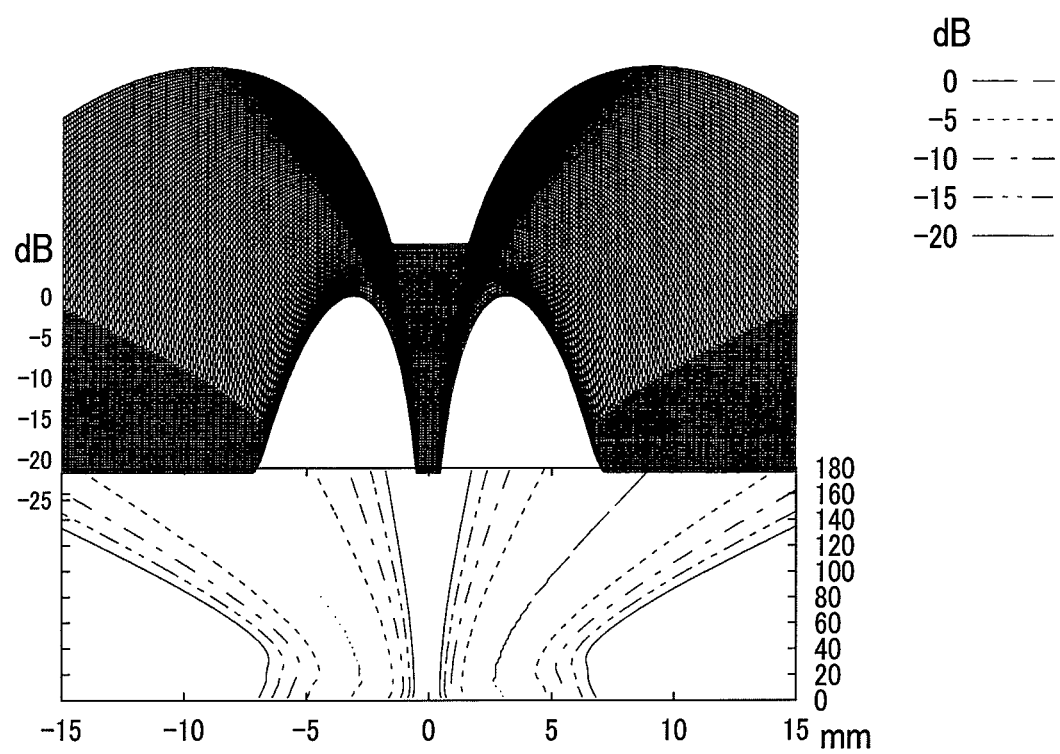
FIG. 10 is a diagram showing an ultrasonic wave intensity distribution in a propagation distance direction in a section of a diagonal line of a transmission beam for the sector scan in the case of performing three-dimensional imaging using a two-dimensional array transducer according to the invention.
Figure 11:
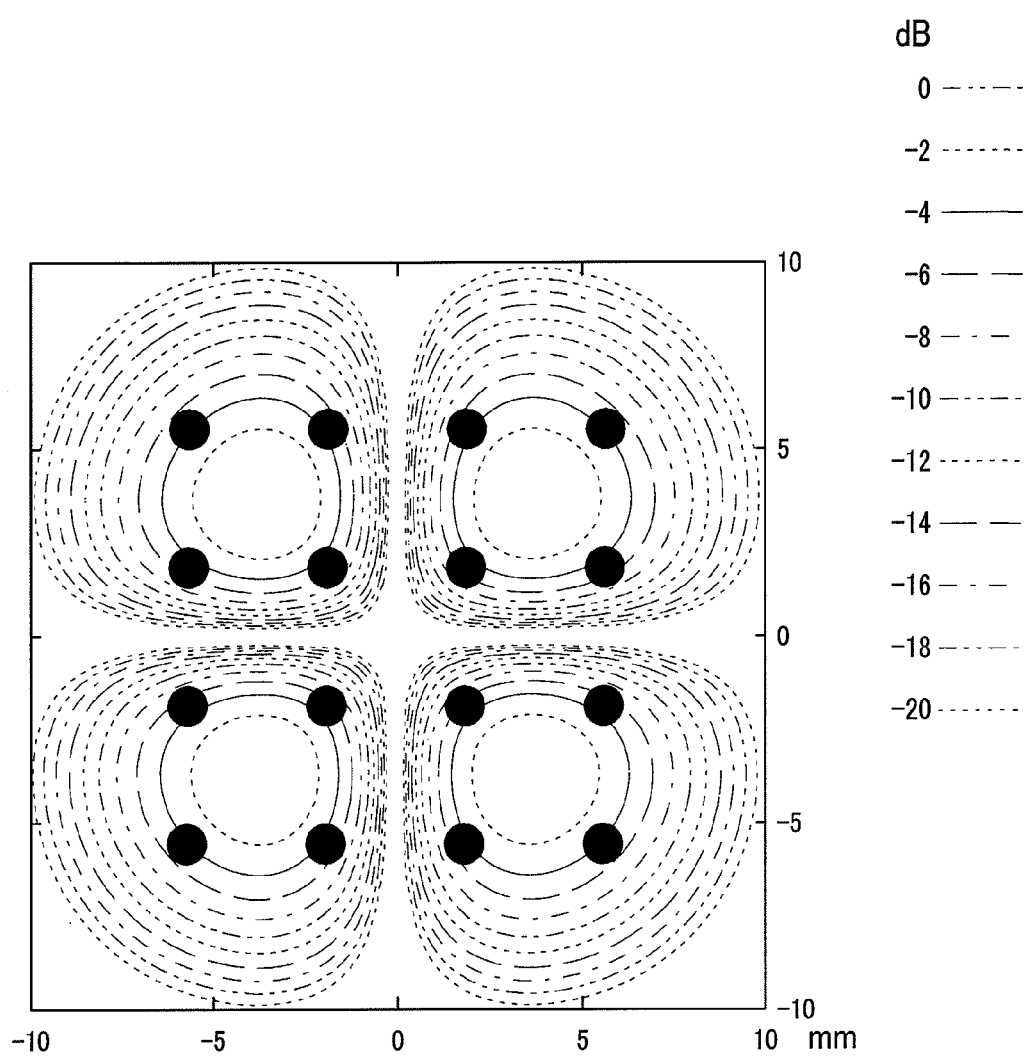
FIG. 11 is a diagram showing positional relations of four lobes generated in the case of performing three-dimensional imaging using the two-dimensional array transducer according to the invention and 16 transmission/reception beams having equal transmission sensitivity.

1 . . . ultrasonic transducer array
2 . . . transmit/receive selection switches
3 . . . transmission beam former
4 . . . selector for transmission delay time and weighting function
5 . . . memory of transmission data time and weighting function
10 . . . receiving beam former
11 . . . filter
12 . . . envelope detector 13 ... scan converter
14 ... display

The invention claimed is:

1. An ultrasonographic device for imaging the inside of an examinee, comprising:
transmission means configured to transmit an ultrasonic pulse signal from a transmission aperture of an ultrasonic element array to an examinee, the transmission means being configured to apply weighting to the transmission aperture of the ultrasonic element array using a Gaussian function, and to control a local focal length of the ultrasonic element array using a Lorentz function during one scanning period; and
reception means which receives the ultrasonic pulse reflected from the examinee,
wherein the transmission means is configured to tune a combination of: a parameter $\beta$ of a differential said Gaussian function determining a spread of a transmission aperture weight, and a parameter $\alpha$ of the Lorentz function determining tendency of a change in the local focal length, to effect the transmitted ultrasonic pulse signal to contain a plurality of peaks with substantially equal transmission intensity in an azimuth direction,
a locus in a depth direction of each peak from the plurality of peaks is a substantially straight line parallel with scan lines of a sector scan, and
the Lorentz resonance function is expressed as a function of coordinates x and y on an array as follows:

$$f(x, y) = f_1 - \left( \frac{1 + \alpha_1 + \alpha_2}{1 + \alpha_1 x^2 + \alpha_2 y^2} - 1 \right) \frac{f_1 - f_0}{\alpha_1 + \alpha_2}$$

wherein $\alpha 1$ and $\alpha 2$ are parameters of the Lorentz resonance function determining tendency in the local focal length and the Lorentz resonance function is set so that transmission beam widths are made constant in a range from a near local focal length $f_0$ to a far local focal length $f_1$ so it becomes possible to form four lobes parallel with scan lines of the sector scan and to form a predetermined angle.

2. The ultrasonographic device according to claim 1, wherein the transmission means transmits the ultrasonic pulse signal by using a delay time weight for controlling delay time of a drive signal for driving any of ultrasonic elements constructing the transmission aperture so that a wave front of the ultrasonic pulse signal transmitted from the transmission aperture has a non-cylindrical shape or an aspherical shape, and an amplitude weight which controls a signed amplitude of a drive signal for driving the ultrasonic element array so as to form a plurality of focal points on each of focal planes in positions of a corresponding plurality of focal lengths.

3. The ultrasonographic device according to claim 2, wherein the transmission means controls a wave front of the ultrasonic pulse signal transmitted from the transmission aperture so that curvature of a center portion in the transmission aperture becomes greater than that of the portion other than the center portion.

4. The ultrasonographic device according to claim 1, wherein the ultrasonic pulse signal having the peaks each drawing a locus, which is substantially a straight line is a group of parallel straight lines in a linear scan, a group of radial straight lines having a common intersecting point at one end of the imaging range in a sector scan, and a group of radial straight lines having a common intersecting point on the outside of the imaging range in a convex scan.

5. The ultrasonographic device according to claim 1, wherein with an ultrasonic pulse signal transmitted from the transmission aperture of the ultrasonic element array to the examinee, four transmission/reception beams having substantially equal transmission intensity in the azimuth direction are generated per transmission beam where the ultrasonic element array is a one-dimensional array, and 16 transmission/reception beams having substantially equal transmission intensity in the azimuth direction are formed per transmission beam where the ultrasonic element array is a two-dimensional array.

6. An ultrasonographic device for imaging the inside of an examinee, comprising:
transmission means configured to transmit an ultrasonic pulse signal from a transmission aperture of an ultrasonic element array to an examinee, the transmission means being configured to apply weighting to the transmission aperture of the ultrasonic element array using a Gaussian function and to control a local focal length of the ultrasonic element array using a Lorentz function during one scanning period; and
reception means which receives the ultrasonic pulse reflected from the examinee,
wherein the transmission means is configured to tune a combination of: a parameter $\beta$ of a differential said Gaussian function determining a spread of a transmission aperture weight, and a parameter $\alpha$ of the Lorentz function determining tendency of a change in the local focal length, to effect the transmitted ultrasonic pulse signal to contain a plurality of peaks with substantially equal transmission intensity in an azimuth direction, and a locus in a depth direction of each peak from the plurality of peaks is a substantially straight line parallel with scan lines of a sector scan; and
wherein the transmitted ultrasonic pulse signal contains at least four peaks with substantially equal transmission intensity in an azimuth direction per transmission beam, and a locus in a depth direction of each peak from the at least four peaks is a substantially straight line parallel with scan lines of a sector scan, and
the Lorentz resonance function is expressed as a function of coordinates x and y on an array as follows:

$$f(x, y) = f_1 - \left( \frac{1 + \alpha_1 + \alpha_2}{1 + \alpha_1 x^2 + \alpha_2 y^2} - 1 \right) \frac{f_1 - f_0}{\alpha_1 + \alpha_2}$$

wherein $\alpha 1$ and $\alpha 2$ are parameters of the Lorentz resonance function determining tendency in the local focal length and the Lorentz resonance function is set so that transmission beam widths are made constant in a range from a near local focal length $f_0$ to a far local focal length $f_1$, so it becomes possible to form four lobes parallel with scan lines of the sector scan and to form a predetermined angle.

7. The ultrasonographic device according to claim 6, wherein the ultrasonic pulse signal having the peaks each drawing a locus, which is substantially a straight line, comprises a group of parallel straight lines in a linear scan, a group of radial straight lines having a common intersecting point at one end of an imaging range in a sector scan, and a group of radial straight lines having a common intersecting point on an outside of the imaging range in a convex scan.

* * * * *